(12) United States Patent
Johnsen et al.

(10) Patent No.: US 11,484,296 B2
(45) Date of Patent: Nov. 1, 2022

(54) ENDOSCOPE

(71) Applicant: AMBU A/S, Ballerup (DK)

(72) Inventors: Lasse Markworth Johnsen, Birkerød (DK); Jesper Mads Bartroff Frederiksen, Vedbæk (DK); Morten Sørensen, Ballerup (DK)

(73) Assignee: AMBU A/S, Ballerup (DK)

( * ) Notice: Subject to any disclaimer, the term of this patent is extended or adjusted under 35 U.S.C. 154(b) by 507 days.

(21) Appl. No.: 16/610,430

(22) PCT Filed: May 2, 2018

(86) PCT No.: PCT/DK2018/050088
§ 371 (c)(1),
(2) Date: Nov. 1, 2019

(87) PCT Pub. No.: WO2018/202267
PCT Pub. Date: Nov. 8, 2018

(65) Prior Publication Data
US 2021/0186469 A1  Jun. 24, 2021

(30) Foreign Application Priority Data

May 2, 2017 (DK) .......................... PA 2017 70294

(51) Int. Cl.
*A61B 1/00* (2006.01)
*A61B 1/015* (2006.01)
(Continued)

(52) U.S. Cl.
CPC ...... *A61B 10/0045* (2013.01); *A61B 1/00094* (2013.01); *A61B 1/015* (2013.01); *A61B 1/2676* (2013.01)

(58) Field of Classification Search
CPC ............ A61B 1/00094; A61B 10/0045; A61B 1/00137; A61B 1/015
See application file for complete search history.

(56) References Cited

U.S. PATENT DOCUMENTS

| 3,735,751 A | 5/1973 | Katz |
| 4,643,197 A | 2/1987 | Greene et al. |
| (Continued) | | |

FOREIGN PATENT DOCUMENTS

| CN | 1177742 C | 12/2004 |
| CN | 101371772 A | 2/2009 |
| (Continued) | | |

OTHER PUBLICATIONS

International Preliminary Report on Patentability received for PCT Patent Application No. PCT/DK2018/050088, dated Nov. 14, 2019, 9 pages.

(Continued)

*Primary Examiner* — Aaron B Fairchild
(74) *Attorney, Agent, or Firm* — Faegre Drinker Biddle & Reath LLP

(57) ABSTRACT

An endoscope (1) having a suction channel and a suction connector in communication with said suction channel, and a working channel through which a liquid may pass. A valve for diverting the suction through the sampling device through a sample container is provided. The endoscope (1) further includes an actuator (7) for propelling the liquid through said working channel.

21 Claims, 5 Drawing Sheets

(51) Int. Cl.
*A61B 1/267* (2006.01)
*A61B 10/00* (2006.01)

(56) References Cited

U.S. PATENT DOCUMENTS

| | | | |
|---|---|---|---|
| 4,760,838 A | 8/1988 | Fukuda | |
| 4,765,312 A | 8/1988 | Sasa et al. | |
| 4,870,975 A | 10/1989 | Cronk et al. | |
| 5,312,332 A | 5/1994 | Bales et al. | |
| 5,347,991 A | 9/1994 | Nakao et al. | |
| 5,363,860 A | 11/1994 | Nakao et al. | |
| 5,409,013 A | 4/1995 | Clement | |
| 5,505,210 A | 4/1996 | Clement | |
| 5,725,478 A | 3/1998 | Saad | |
| 5,800,414 A | 9/1998 | Cazal | |
| 6,017,316 A | 1/2000 | Ritchart et al. | |
| 6,022,334 A | 2/2000 | Edwards et al. | |
| 6,190,330 B1 | 2/2001 | Harhen | |
| 6,325,785 B1 | 12/2001 | Babkes et al. | |
| 6,331,165 B1 | 12/2001 | Turturro et al. | |
| 6,375,625 B1 * | 4/2002 | French | A61B 10/0045 600/573 |
| 6,632,182 B1 | 10/2003 | Treat | |
| 6,679,834 B2 | 1/2004 | Stahl et al. | |
| 6,840,909 B2 | 1/2005 | Gatto | |
| 6,852,108 B2 | 2/2005 | Barry et al. | |
| 7,065,940 B2 | 6/2006 | Dudek et al. | |
| 7,172,579 B2 | 2/2007 | Barzell et al. | |
| 7,479,257 B2 | 1/2009 | Nguyen et al. | |
| 7,708,938 B2 | 5/2010 | Mariotti et al. | |
| 7,806,835 B2 | 10/2010 | Hibner et al. | |
| 7,921,876 B2 | 4/2011 | Wright et al. | |
| 8,062,286 B2 | 11/2011 | Shippert | |
| 8,262,565 B2 | 9/2012 | Okada | |
| 8,287,500 B2 | 10/2012 | Baba et al. | |
| 8,382,660 B2 | 2/2013 | Okada | |
| 8,460,182 B2 | 6/2013 | OuYang et al. | |
| 8,632,498 B2 | 1/2014 | Rimsa et al. | |
| 8,870,756 B2 | 10/2014 | Maurice | |
| 9,204,868 B2 | 12/2015 | Furlong et al. | |
| 9,332,969 B2 | 5/2016 | Han et al. | |
| 9,339,172 B2 | 5/2016 | Slenker et al. | |
| 9,408,593 B2 | 8/2016 | Furlong et al. | |
| 9,421,001 B2 | 8/2016 | Speeg et al. | |
| 9,486,185 B2 | 11/2016 | Hibner | |
| 9,486,186 B2 | 11/2016 | Fiebig et al. | |
| 9,498,193 B2 | 11/2016 | Smith et al. | |
| 9,538,994 B2 | 1/2017 | Hibner et al. | |
| 9,545,244 B2 | 1/2017 | Parihar et al. | |
| 9,603,587 B2 | 3/2017 | Fiebig et al. | |
| 9,737,285 B2 | 8/2017 | Fiebig et al. | |
| 9,808,146 B2 | 11/2017 | Furlong | |
| 9,913,629 B1 | 3/2018 | Sullivan et al. | |
| 9,943,291 B2 | 4/2018 | VanDerWoude et al. | |
| 9,987,439 B2 | 6/2018 | Williams, Jr. et al. | |
| 10,046,288 B2 | 8/2018 | Wang et al. | |
| 10,624,531 B2 | 4/2020 | Matthison-Hansen | |
| 10,646,107 B2 | 5/2020 | Matthison-Hansen et al. | |
| 10,869,653 B2 | 12/2020 | Keller | |
| 11,357,386 B2 | 6/2022 | Lund et al. | |
| 2002/0082475 A1 | 6/2002 | Stahl et al. | |
| 2003/0167053 A1 | 9/2003 | Taufig | |
| 2003/0216617 A1 | 11/2003 | Hirakui et al. | |
| 2004/0068291 A1 | 4/2004 | Suzuki | |
| 2005/0154262 A1 | 7/2005 | Banik et al. | |
| 2006/0047185 A1 | 3/2006 | Shener et al. | |
| 2006/0224042 A1 | 10/2006 | Jackson et al. | |
| 2006/0229498 A1 | 10/2006 | Kohno | |
| 2006/0252993 A1 | 11/2006 | Freed et al. | |
| 2006/0258955 A1 | 11/2006 | Hoffman et al. | |
| 2007/0027359 A1 | 2/2007 | Salman | |
| 2007/0043262 A1 | 2/2007 | Levy et al. | |
| 2007/0049796 A1 | 3/2007 | Fujikura | |
| 2007/0179341 A1 | 8/2007 | Okada | |
| 2007/0179407 A1 | 8/2007 | Gordon et al. | |
| 2007/0213590 A1 | 9/2007 | Squicciarini | |
| 2007/0213632 A1 | 9/2007 | Okazaki et al. | |
| 2007/0255256 A1 | 11/2007 | Fischer et al. | |
| 2007/0270714 A1 * | 11/2007 | Cushner | A61B 10/04 600/571 |
| 2008/0021280 A1 | 1/2008 | Suzuki | |
| 2008/0027283 A1 | 1/2008 | Matsui et al. | |
| 2008/0033290 A1 | 2/2008 | Saadat et al. | |
| 2008/0058650 A1 | 3/2008 | Saadat et al. | |
| 2008/0082021 A1 | 4/2008 | Ichikawa et al. | |
| 2008/0163669 A1 | 7/2008 | Gregory et al. | |
| 2008/0183037 A1 | 7/2008 | Ichikawa et al. | |
| 2008/0255424 A1 | 10/2008 | Durgin et al. | |
| 2008/0287920 A1 | 11/2008 | Fangrow et al. | |
| 2009/0209478 A1 | 8/2009 | Nakayama et al. | |
| 2009/0209821 A1 | 8/2009 | Yamane | |
| 2009/0247880 A1 | 10/2009 | Naruse et al. | |
| 2009/0306545 A1 | 12/2009 | Elsakka et al. | |
| 2011/0105839 A1 | 5/2011 | Hoffman et al. | |
| 2011/0169260 A1 | 7/2011 | Lin et al. | |
| 2011/0245606 A1 | 10/2011 | Hayashi et al. | |
| 2012/0089164 A1 | 4/2012 | Kojima et al. | |
| 2012/0095369 A1 | 4/2012 | Teixeira | |
| 2012/0116296 A1 | 5/2012 | Ducharme et al. | |
| 2012/0157770 A1 | 6/2012 | Williams, Jr. et al. | |
| 2012/0289858 A1 | 11/2012 | OuYang et al. | |
| 2013/0079702 A1 | 3/2013 | Klein et al. | |
| 2013/0122453 A1 | 5/2013 | Paxton | |
| 2013/0123663 A1 | 5/2013 | Hibner et al. | |
| 2013/0267777 A1 | 10/2013 | Avitsian et al. | |
| 2014/0088460 A1 | 3/2014 | Teixeira et al. | |
| 2014/0121560 A1 | 5/2014 | Parks | |
| 2014/0187859 A1 | 7/2014 | Leeuw et al. | |
| 2014/0360494 A1 | 12/2014 | Herskovic | |
| 2014/0378864 A1 | 12/2014 | Hibner | |
| 2015/0018711 A1 | 1/2015 | Furlong et al. | |
| 2015/0065912 A1 | 3/2015 | Peliks | |
| 2015/0122294 A1 | 5/2015 | Wang et al. | |
| 2015/0182105 A1 | 7/2015 | Salman et al. | |
| 2015/0209491 A1 | 7/2015 | Cushner et al. | |
| 2015/0327875 A1 | 11/2015 | Look et al. | |
| 2016/0220102 A1 | 8/2016 | Shener-Irmakoglu et al. | |
| 2016/0256139 A1 | 9/2016 | Hadley et al. | |
| 2017/0100149 A1 | 4/2017 | Todd | |
| 2017/0274125 A1 | 9/2017 | Minskoff et al. | |
| 2018/0092633 A1 | 4/2018 | Peliks | |
| 2019/0133564 A1 | 5/2019 | Kirkemo | |

FOREIGN PATENT DOCUMENTS

| | | |
|---|---|---|
| CN | 204932566 U | 1/2016 |
| CN | 105342545 A | 2/2016 |
| DE | 10 2010 474 34 | 4/2012 |
| JP | 2003310540 A | 11/2003 |
| WO | 2004020019 A2 | 3/2004 |
| WO | 2010027109 A1 | 3/2010 |
| WO | 2014028366 A1 | 2/2014 |
| WO | WO 2016/188540 | 12/2016 |

OTHER PUBLICATIONS

International Search Report and Written Opinion from corresponding Application No. PCT/DK2018/050088, dated Jul. 3, 2018.
Danish Search Report from corresponding Application No. PA 2017 70294, dated Aug. 4, 2017.

* cited by examiner

ENDOSCOPE

CROSS-REFERENCE TO RELATED APPLICATIONS

This application is a National stage application filed under 35 U.S.C. § 371 of International Application No. PCT/DK2018/050088, filed on May 2, 2018, which claims the benefit of Denmark Patent Application No. PA 2017 70294, filed on May 2, 2017, which applications are incorporated herein by reference in their entirety.

TECHNICAL FIELD

The present invention relates to an endoscope, more specifically to an endoscope having a suction channel, a suction connector in communication with said suction channel, and a working channel through which a liquid may pass.

BACKGROUND

Endoscopes with sampling devices are inter alia used in procedures such as bronchial lavage (BL), bronchial wash (BW) or bronchoalveolar lavage (BAL) which are commonly used procedures for obtaining samples of organic material from a lung segment of a patient. This is basically done by flushing a lung segment with sterile water, normally a sterile aqueous saline solution, and then sucking the water into a sample container. More specifically the distal end of an endoscope is advanced to the location in the lung where the sample is to be taken. In bronchoalveolar lavage, the distal end is then pressed into firm engagement against the interior of the lung to help securing the position in a process commonly referred to as wedging.

Via the working channel of the endoscope, sterile water, e.g. a 0.9% saline solution, is instilled into the lung at the sample location and as much as possible extracted again, now containing organic material, and thus constituting a sample. Typically, this is done by attaching a filled syringe of a volume between 20 ml and 60 ml, e.g. 50 ml to the working channel of the endoscope, via a communication port in endoscope handle. The syringe is then used for each instillation as well as the subsequent extraction. This process is normally repeated several times in a row with new syringes, e.g. three to four, the samples being suitable for various purposes, depending which number of sample in the sequence they are, because the composition of the organic material varies. If the syringe is used for extraction, the sample would be transferred to a sample container suitable for securing biological material. Upon extraction the sample containers are therefore normally labelled accordingly.

As an alternative to the extraction using the syringe, the extraction may be performed using an external suction and a Lukens trap, e.g. as disclosed in U.S. Pat. No. 4,643,197.

Using a Lukens trap attached to the endoscope in the manner disclosed in U.S. Pat. No. 4,643,197, i.e. interposed in the flexible suction line leading from the endoscope to the vacuum or suction source (the two terms are considered to be synonyms throughout this description), involves several disadvantages when carrying out the procedure. One such disadvantage is that being suspended on the line the operator has only little sense of and attention to the orientation of the trap, as the operators visual focus is on the monitor the major part of the attention is on other part of the procedure e.g. the delicate parts of the procedure within the patient. It therefore does happen that the Lukens trap inadvertently ends up in an orientation where the sample is lost, because it gets sucked out of the trap by the vacuum source or suction. Another disadvantage is that there is a lot of work involved in connecting and disconnecting tubes as well as other parts, if e.g. the operator needs to change between obtaining a sample and suction in order to clean without sampling.

A further problem is that if the syringe is connected to the working channel where the entry port is located at the proximal end of the endoscope handle the aggregate height of the handle and syringe is quite high—in particular if a Luer lock adapter is interposed and the plunger of the syringe is not yet depressed, leading to instability and lack of handiness when the plungerrod of the syringe is to be operated.

SUMMARY OF DISCLOSED EMBODIMENTS

Based on this, it is the object of the present invention to provide an endoscope which renders itself for the use in sampling procedures, such as the BL, BW and BAL procedures mentioned above, and which does not suffer from the above drawbacks.

According to a first aspect of the invention this object is achieved by an endoscope according to the opening paragraph, which comprises a sampling device through which suction may be applied to the working channel, and a valve for diverting the suction applied through the sampling device so that the suction is diverted though a sample container.

By providing the endoscope with the sampling device, preferably as an integral part of the endoscope, or at least rigidly connected thereto it is less likely that the operator brings the sample container into an orientation where the sample is lost. This is because the orientation is immediately linked to the orientation of the endoscope handle, for which the operator has a clear sense as he is gripping it with his hand.

According to a second aspect of the invention the object is achieved by a method for performing a lavage comprising the steps of providing an endoscope according to an embodiment of the first aspect of the invention, connecting the sampling device to a vacuum source, inserting an insertion part of the endoscope into a body cavity, administering a saline solution through the endoscope to the body cavity, collecting a sample by drawing fluid from the body cavity through the endoscope and a sample container.

According to a third aspect of the invention, the object is achieved with a kit comprising an endoscope according to an embodiment of the first aspect of the invention, a saline cartridge or a syringe for saline, at least one sample container.

According to a preferred embodiment of the first aspect of the invention, the endoscope comprises a sample container connector adapted for connecting the sample container. This allows easy replacement of sample containers, when as is normal, several samples are taken in sequence.

According to a further embodiment, at least a part of the suction channel and at least a part of the working channel are provided as one and the same channel section. This allows the use of at least a part of the same channel for dual purposes, more specifically the part located in the insertion tube where space is sparse, in turn freeing the space that would be occupied by one channel if two separate channels were used.

According to another preferred embodiment, the actuator for propelling the liquid through said working channel comprises a digitally displaceable (i.e. displaceable by the fingers) actuator adapted to provide a force displacing the liquid. Using a digitally displaceable actuator has the advantage that the operator is provided with direct tactile feedback on amount and pressure of the liquid instilled, when the digitally displaceable actuator is in a direct kinematic connection with e.g. a piston. Moreover, no external energy supply or pre-pressurization of the liquid is necessary.

According to a further preferred embodiment, the liquid is contained in a liquid container comprising a displaceable piston adapted to displace the liquid under the influence of the force provided by the actuator. This is a simple and efficient way of propelling the liquid, in particular when there is no pre-pressurization.

According to yet another embodiment, the digitally displaceable actuator is connected to a force transmitting kinematic chain adapted to transfer motion and force between the digitally displaceable actuator and the displaceable piston. Such a kinematic chain gives the operator a direct tactile feedback, and allow a matching of the full displacement of the displaceable actuator and the total volume of the liquid container. A simple and preferred way of providing such a force transmitting kinematic chain is a rack and pinion arrangement.

According to a further embodiment the liquid container is an integral part of the endoscope. This provides advantages over interchangeable liquid containers, when it comes to sealing, and if the liquid container is filled at the manufacturing stage. Furthermore, it provides a dedicated singleuse endoscope for BL, BW or BAL procedures.

According to another embodiment, the endoscope comprises an actuator for propelling the liquid through said working channel. With an actuator for propelling the liquid through the working channel, it becomes much easier for the operator to instill the liquid into the lungs of the patient. With a suitable selected location of the actuator on the handle of the endoscope, it even becomes possible to instill the liquid using the same hand as is used for maneuvering the endoscope and activating suction, thus freeing the operator's other hand or a hand of the assisting personnel to other purposes.

According to a preferred embodiment, the endoscope comprises a valve actuator adapted to be operated using a single finger of a hand of the operator and located in a position on the endoscope where it is accessible and operable by the finger of the hand of an operator with which the operator is gripping the endoscope. This allows the valve actuator to be operated by the operator himself without having to release the grip on the endoscope and removing the hand from the handle, using another hand or relying on additional personnel. This, in turn, facilitates the procedure and keeps number of personnel involved down.

According to another preferred embodiment, the endoscope is adapted for single use. This allows the sampling device to be constructed from low cost materials such as plastics, because it needs not be able to withstand the harsh circumstances of cleaning and sterilization, such as the high temperatures of an autoclave.

BRIEF DESCRIPTION OF THE DRAWINGS

The invention will now be described in greater detail based on non-limiting exemplary embodiments, and with reference to the drawings on which.

DETAILED DESCRIPTION

Figure 1:
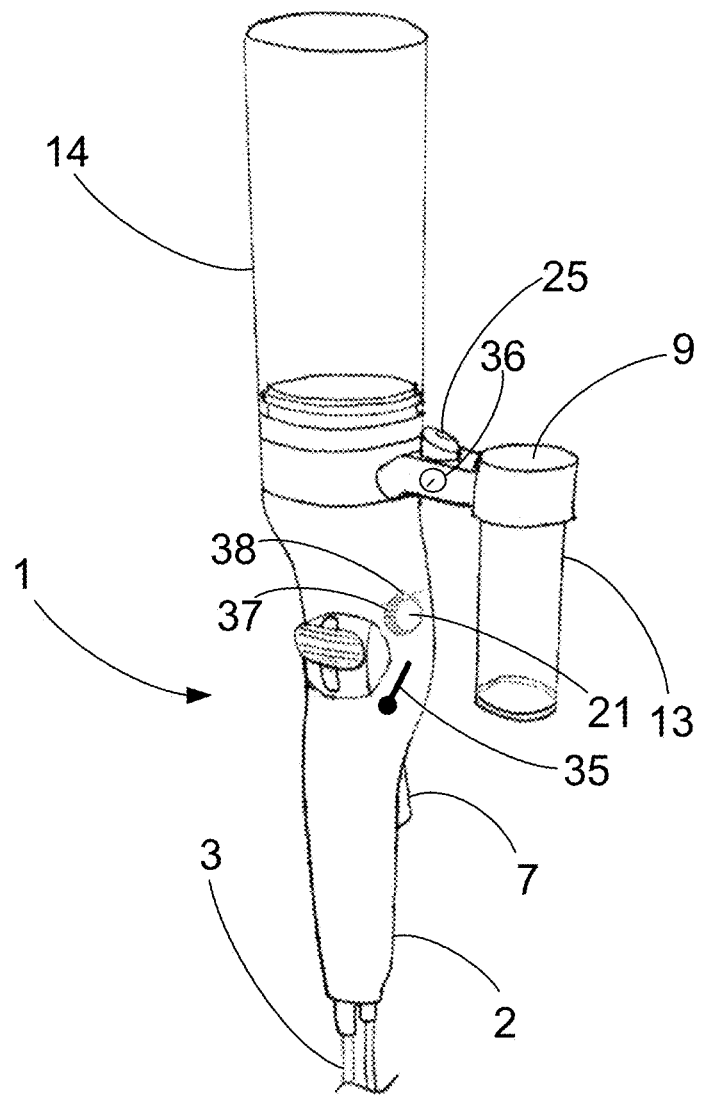
FIG. 1 shows a perspective view of an endoscope according to the present invention with irrelevant parts of the insertion tube and the connection cable removed for illustration purposes.

Turning first to FIG. 1 an endoscope 1 having a handle 2 and an insertion tube 3 is shown. For illustration purposes, the insertion tube 3 is only shown in part in FIG. 1 as well as in the schematic FIGS. 2 and 3. For the purposes of this description the insertion tube 3 defines a longitudinal direction of the endoscope 1. At the distal end of the insertion tube 3 an articulated bending section allowing the insertion tube to be maneuvered trough the body cavities. In the present description where the outset is bronchial or bronchoalveolar lavage or bronchial wash, such body cavities would include trachea and bronchi of the patient, but as will be appreciated by the skilled person the use of the sampling device according to the present invention is not limited to these procedures. The distal tip of the bending section comprises openings connected to one or more channels at least one of which, such as the working channel 19, may be used as a suction channel. The suction channel may be connected to a suction or vacuum source at a connector 4, shown only schematically in FIGS. 2 and 3, by the activation of a valve operated by a push-button 5 on the handle 2 of the endoscope 1 in a well-known manner. As is also well known, the distal tip furthermore includes a light source and a camera connected via a cable to a monitor allowing the operator and others to monitor the actions performed within the patient.

The connector 4 is of a standard type for attaching a flexible suction tube 8, in turn connected to a vacuum or suction source, e.g. the wall suction normally found in hospitals. The connector 4 is generally tubular with a taper to allow easy connection of the flexible suction tube 8 and with circumferential corrugations or barbs allowing a secure connection of the flexible suction tube 8 in a well-known manner.

Figure 4A:
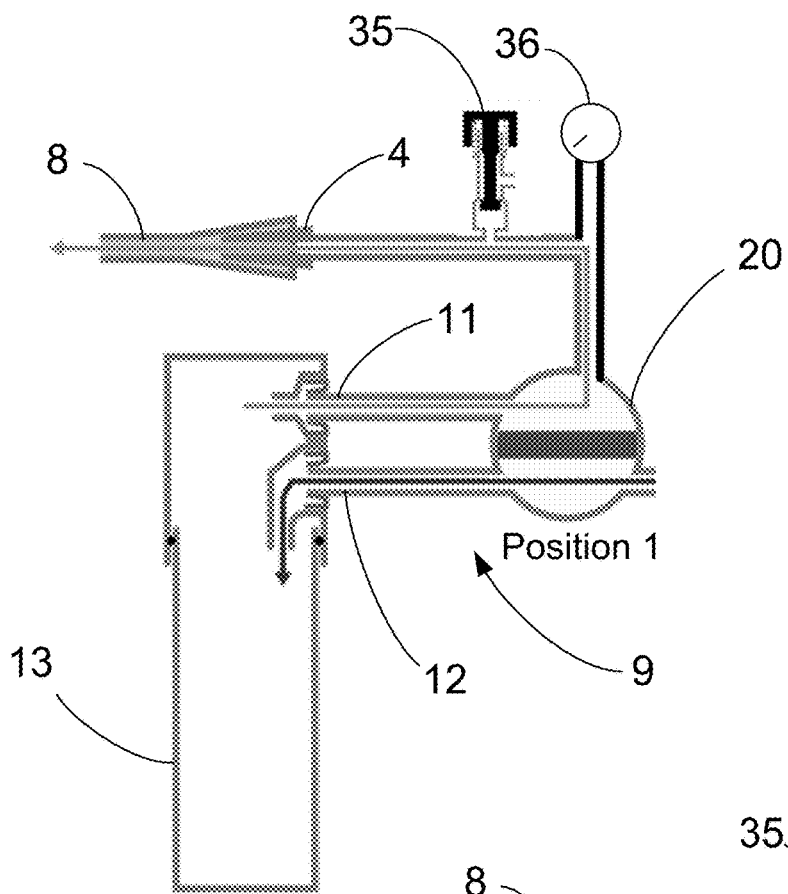
FIGS. 4a and 4b are schematic diagrams showing possible flow paths in connection with the sampling system of the embodiment of FIG. 2.
Figure 4B:
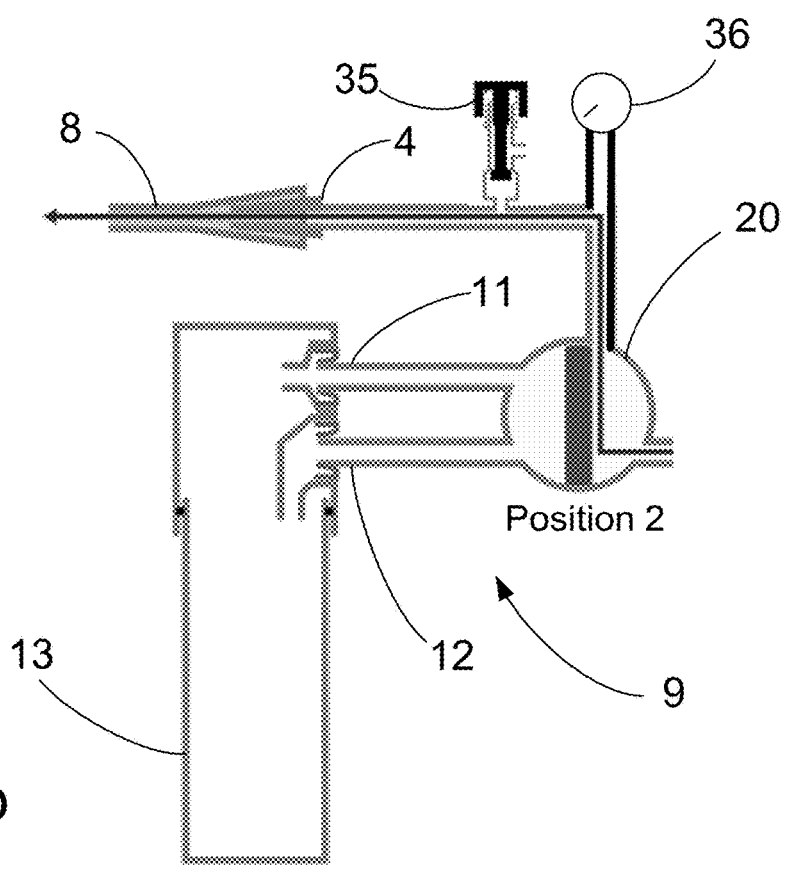
Figure 5:
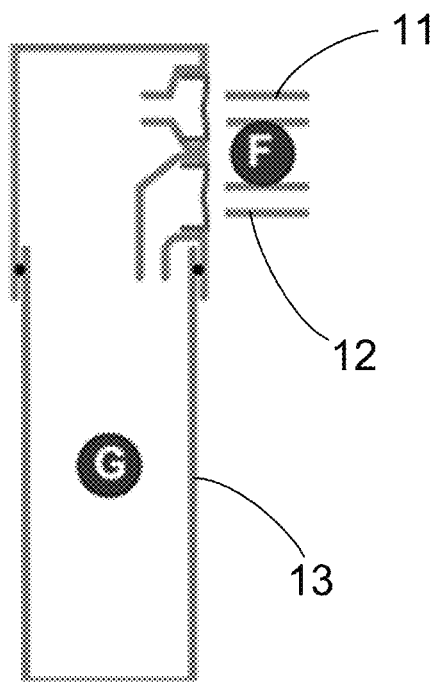
FIG. 5 is a schematic illustration of a detached sample container.

However, rather than connecting the flexible suction tube 8 directly to the suction channel 19, a sampling device 9 shown schematically in FIGS. 4a and 4b is interposed so that the sampling device is connected to the flexible suction tube 8. The sampling device is preferably an integral part of the endoscope 1, in particular of the handle 2 thereof, but the sampling device 9 could be a separate part attachable to the endoscope 1 and having a receptacle for receiving a standard connector provided on the handle, i.e. a connector identical, similar or at least corresponding to the connector 4 to which the flexible suction tube 8 is be attached in FIG. 2. The sampling device 9 furthermore comprises a sample container 13 and a sample container connector comprising a pair of tubular protrusions 11, 12 adapted to engage and be inserted through the wall of a preferably detachable sample container 13. Using a pair of tubular protrusion 11, 12 allow the easy penetration of a suitable sealing, such as lip seals on the sample container 13. Such seals may be made from an elastomer membrane, e.g. a rubber like material. The membrane comprises an aperture or slit sealed by the material. FIG. 5 schematically shows a detachable sample container 13 in a situation where it is detached from the sampling device 9. Preferably, the sample container is adapted to self-seal the openings through which the tubular protrusions 11, 12 passes, when the protrusions are not present in the openings, i.e. when the sample container 13 is detached from the sampling device 9. I.e. the membrane seals the aperture or slit when protrusions are not present, and when the protrusions are present the membrane seals tightly around the protrusions. This allows the extraction of several samples one after the other by simple removal and replacement of the filled sample container 13 with a new and empty one. Since the sample container 13 self-seals, the risk of contamination of not only the sample in the container but also the surroundings, e.g. personnel. The handling of the samples is thus facilitated, as the personnel needs to care less about contamination. This allows the personnel to focus their attention on other parts of the procedure, in turn, facilitating the overall procedure.

The tubular protrusions 11, 12 are preferably arranged in such a manner on the sampling device 9 that they extend in a direction transversely to the longitudinal direction of the endoscope 1. In this illustrated embodiment where the connector 4 extends itself transversely to the longitudinal direction of the endoscope, this means that the tubular protrusions 11, 12 of the sample container connector extend transversely to the longitudinal direction of the endoscope 1. This has the advantage that displacements, such as jerks when detaching or attaching the sample container 13 will mainly be in the transverse direction to the endoscope 1 and therefore be less likely to cause any displacement of the endoscope in the longitudinal direction, i.e. the aforementioned endoscope insertion direction. Such longitudinal displacement is undesired as the displacement could cause the tip of the endoscope to move within the patient, which could result in loss of the wedge position and thereby extend the time for the procedure.

Figure 2:
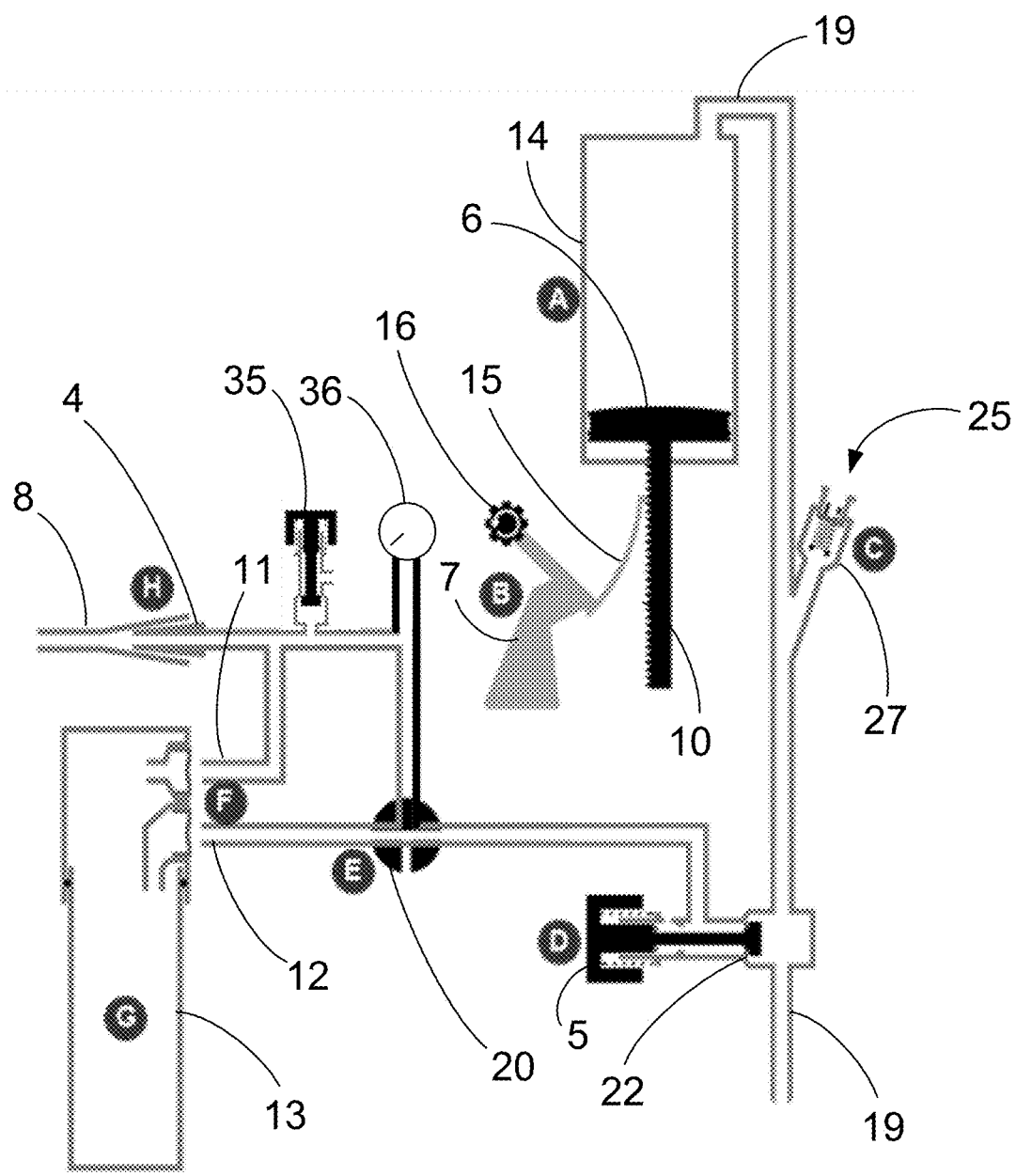
FIG. 2 is a schematic diagram of containers and conduits of the endoscope according to the invention.
Figure 3:
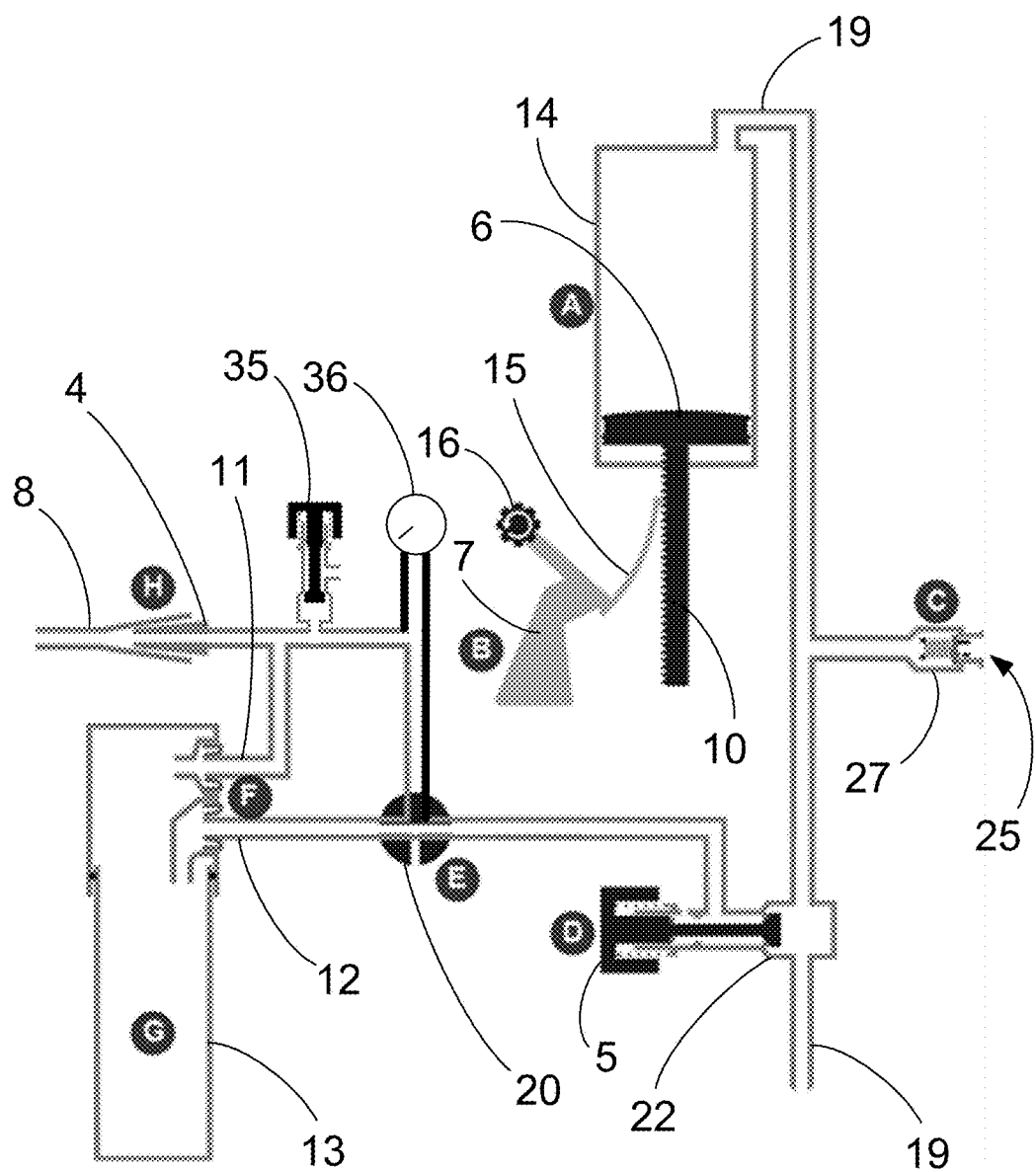
FIG. 3 is a schematic diagram of containers and conduits of an alternative embodiment of an endoscope according to the invention.
Figure 7:
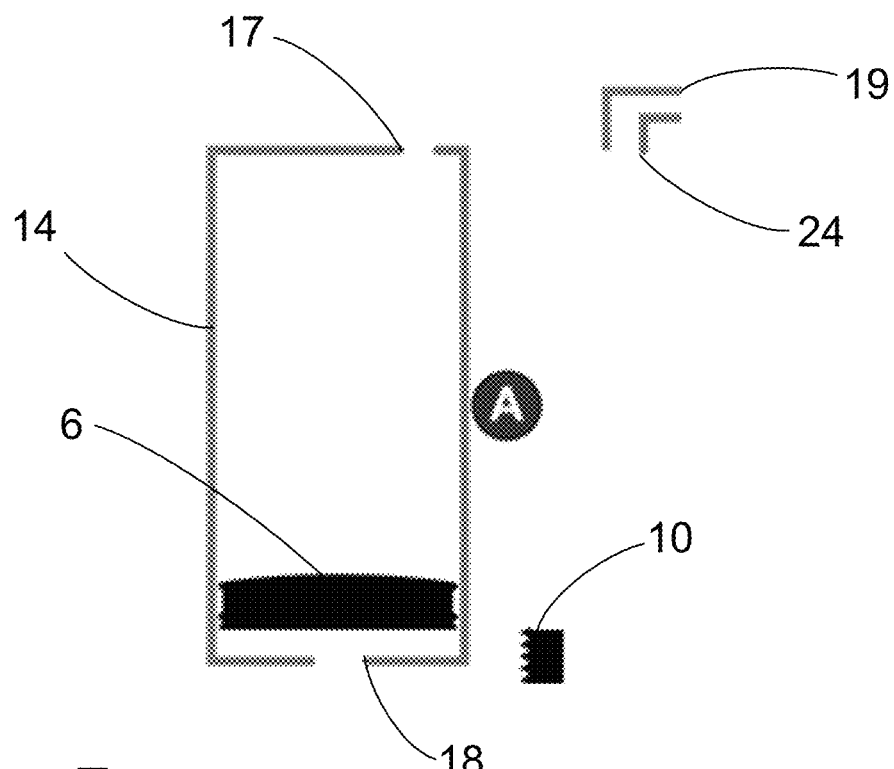
FIG. 7 is a schematic illustration of a detachable cartridge saline container.

Turning now to FIG. 1 again a liquid container 14 can be seen at the proximal end of the endoscope 1. The liquid container 14 may be an interchangeable saline cartridge but could be an integrated part of the endoscope 1. In either case it is in fluid connection with the working channel 19, of the endoscope, as can be seen in FIG. 2. The liquid container 14 is pre-filled with a saline solution but preferably not pressurized, but in the alternative it could be filled at the point of use. Instead a piston 6 as seen in FIGS. 2, 3 and 7 is used as a means for exerting pressure on the saline solution in order to displace it and propel it into the working channel 19. The piston 6 is operated by an actuator 7 such as a hinged push-button or trigger located in such a way on the endoscope that it is digitally operable by the operator, e.g. by the index finger. The force and exerted by the operator on the actuator is transferred to the piston 6 via a kinematic chain so as to exert a force on the liquid in the liquid container and displace the piston 6 as the liquid is pushed into the working channel 19 and though the working channel 19 into the lungs of the patient, from where it is later to be extracted. The skilled person will appreciate that such a kinematic chain can be devised in numerous ways, but it is currently preferred to use a rack and pinion arrangement. Thus the piston rod 10 comprises a toothing over at least a part of the length thereof. This toothing meshes with one or more teeth of a pinion 15 connected to the actuator 7. Thus when the actuator 7 is depressed it turns over an angle about the hinge axis 16, thereby displacing the piston rod 10 and the piston 6. When the piston 6 acts on the saline solution to expel it, the operator may control the volume of liquid expelled by the degree and the speed with which he depresses the actuator 7. Due to the kinematic chain the operator has immediate tactile feedback to index or whichever finger(s) used, regarding the volume, speed and pressure of liquid being dispensed into the working channel 19, and via the working channel instilled at the desired location in the patient at the tip of the endoscope 1.

Though not currently preferred, the liquid container 14 could of course be pre-pressurized, e.g. using pre-tensioned biasing spring acting on the piston 6, or by use of a bladder filled with compressed air or gas located in the liquid container 14. In that case the actuator 7 would be acting on a release valve. Though this may have some advantages, e.g. that the operator needs to provide less force to the actuator 7, it does not necessarily convey the same sense of force and volume of the instilled liquid.

Having instilled the saline solution in the patient a liquid sample can now be extracted using the parts comprising the endoscope 1, the sampling device 9, the sample container 13 and the flexible suction tube 8 to the vacuum or suction source.

To do so, the operator or another suitable person in the team turns a valve 20 such as a shunt valve (FIG. 2) or a three-way valve (FIG. 3) via a valve actuator 21, such as knob or the like to the position shown in FIG. 4a ("Position 1"), to establish a fluid passage from the tubular protrusion 12 through the sampling device 9. Preferably, the valve actuator 21 is located in a position on said endoscope 1 which is accessible by a hand of an operator with which the operator is gripping the handle 2 of the endoscope 1. The valve actuator 21 may be located on a side of the endoscope 1 where it can be seen by the operator and operated by the thumb of the operator (see FIG. 1). It is however, not excluded that it may be located elsewhere and operated by another finger, e.g. on the opposite side of what is shown in FIG. 1 and operated with the index finger. In either case, the valve actuator 21 is adapted to be operated by a single finger of the operator. Since the endoscope 1 itself is intended as a disposable device, i.e. single use device to be thrown away after the sampling procedure, it is easy to adapt the valve actuator 21 to be operable with a single finger. More specifically, the valve actuator may be provided with grooves 37 between and/or protrusions 38 allowing for good friction, because such grooves 37 and/or protrusions need not be cleaned and sterilized after use. Likewise, other friction enhancing features could be used, such as knurling and the like.

The operator then presses the push-button 5 opening the valve 22, so as to open a passage through the working or suction channel 19 of the endoscope. Liquid or rather a fluid comprised of air and liquid from the sampling site, e.g. in the lungs, will now be drawn through the working channel 19 to the valve 22, via the valve 22 through the sampling device 9, out of the tubular connector 12 and into the sample container 13. In the sample container 13 the liquid will be trapped, as it falls to the bottom under the influence of gravitation, whereas the remainder, which is mostly air, will be sucked out through the tubular connector 11 and away via the flexible suction tube 8.

To better control and monitor the suction, the endoscope may optionally have a suction reduction valve 35, with which the operator can reduce the amount of suction provided by the vacuum source, and a manometer or other pressure indicator 36. The pressure indicator, if provided, is preferably located in a position on the sampling device 9 where, in use, it is visible by the operator, but any visible place on the endoscope will of course do. It should be noted though, that the pressure indicator 36 is just a further option, and that the pressure reduction valve 35 may be implemented without the pressure indicator 36, and in principle also vice versa. The pressure indicator 36 need not be able to give a detailed reading. Rather, it is envisaged that a simple indication that the pressure is within an acceptable range may suffice.

Both the suction reduction valve 35 and the pressure indicator 36 are also schematically shown in FIGS. 2, 3, 4a and 4b. The actual nature and design of the suction reduction valve 35 may be one of many. It could be a throttling valve adjustable with a screw or similar. It could also be, as indicated in FIG. 1, be a slider covering one or more openings through which false air may be drawn in to reduce the suction pressure. This could be one long opening that is gradually covered, or several smaller holes covered one by one in steps. Especially in case where false air is relied on for suction pressure reduction, the location of the suction reduction valve is preferably between the external connector 4 to the vacuum source and the tubular connector 11, in order not to draw the false air from the ambient air in the environment through the sampling container 13, as this would potentially be a cause for pollution of the sample with pollutants from the ambient environment, which were never in the lungs of the patient. Also, if the latter solution with false air is used, the pressure indicator 36 is preferably located between the suction reduction valve 35 and the tubular connector 11 order to ensure correct reading of the pressure indicator 36.

When a sample of suitable volume has accumulated in the sample container 13, the push-button 5 is released, and the valve 22 closes, as it is biased towards a closed state in a well-known manner, e.g. spring loaded.

Figure 6:
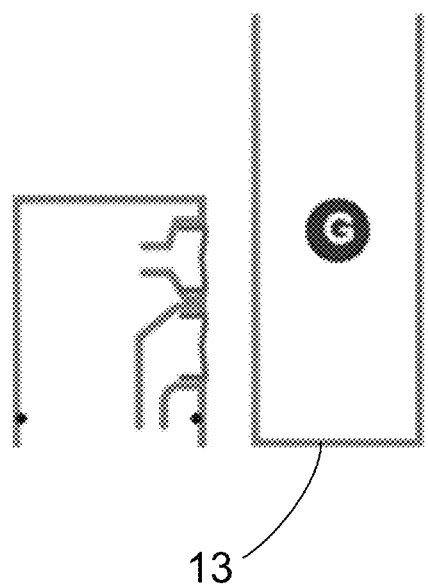
FIG. 6 is a schematic illustration of a two-part detachable sample container.

The sample container may now be removed and possibly replaced with a new and empty one, and the process repeated. As can be seen from FIG. 6 the sample container 13 could be a two-part assembly, so as to allow only to remove the lower receptacle part, leaving the upper top part in place. However, it is currently preferred to have them and remove them as one part, in order to avoid the open receptacle, which will be more prone to contamination, when the top part is not acting as a lid. It may be necessary to divide the sample into other sampling containers, e.g. for the purpose of different specific analysis.

If no more samples need be taken, valve 20 may be turned to the position shown in FIG. 4b ("Position 2") to shunt the passage though the sample container 13 via the tubular connectors 11 and 12. Normal suction of the fluid 23 through the working channel 19 may then be performed without having to remove the sampling container 13, i.e. normal operation with the endoscope, which may be unrelated to the sampling, may still be performed without having first to remove the sampling container 13.

An opening in the sample container is preferably adapted such that the distal end of the endoscope's insertion tube 3 can be entered into the sample container 13 in order to deliver a sample from e.g. the working channel 19 through the distal end of the endoscope. This will be relevant in the event that the working channel, or the channel applied for collecting a sample, is blocked e.g. by mucus, phlegm, blood etc. and the material contained in the working channel is needed as a sample. Traditionally such material has been discarded by applying a pressure from the proximal end of the working channel, e.g. by pressing water (or air) into the working channel by a connected syringe or saline container, while placing the distal end of the insertion cord at a sterile cloth or paper. But in the event that it is not possible to obtain another sample, it would be an advantage if the material in the working channel 19 could be collected in a sample container instead of being discarded.

This can be achieved by entering the distal end of the endoscope into a sample container and then applying the pressure from the proximal end of the working channel. The opening in the sample container for this purpose could be an extra opening (not shown in figures), or it could be an existing opening also applied for the connection to the sampling device 9 through the tubular protrusions 11, 12 of the sample container connector. The opening should preferably be self-sealing to avoid spillage of sample material when the tip of the endoscope's insertion cord has been removed. Also, there should be provided an opening for air pressure to escape from the sample container while the tip of the insertion cord is arranged in the opening. This is to avoid that the applied pressure for removing the blockage from the working channel will also remove the sample container from the tip of the insertion cord in the moment the blockage passes into the sample container.

In practice, the operator of the endoscope should remove the insertion cord from the body cavity and from the body as such, when a blockage of the working channel is identified e.g. when suctioning is blocked. The tip of the insertion cord is inserted into the suitable opening in a sample container, and a syringe is connected to an entrance to the working channel e.g. at the handle of the endoscope. An increasing air pressure is applied to the working channel by the syringe, until the blockage is removed and the material from the working channel enters into the sampling container. The tip of the insertion cord is then removed from the sample container, and may be re-introduced into the body cavity if necessary.

As mentioned the sampling device 9 could be a separate element adapted to engage the endoscope 1, in particular the handle thereof, in a manner preventing rotation about the tubular connector 4. Accordingly, the sampling device 9 would also in that case follow the movements of the endoscope 1, or more specifically the handle 2 of the endoscope 1. Since the operator is used to gripping the handle 2 of the endoscope 1 and familiar with the orientation thereof, the likelihood that the endoscope 1 ends up in an orientation where the sample is lost, will still be reduced even with an attached sampling device 9.

As can be seen from both FIGS. 1 and 2 as well as FIG. 3 the endoscope comprises an inlet 25 for injection of an additional fluid, typically but not exclusively a local anesthetic such as Lidocaine, which may be injected to reduce coughing reflexes in the patient during the procedure. This may be done by attaching a syringe to the inlet 25 in a well-known manner and inject the fluid in a likewise well-known manner. As can be seen by comparison between FIG. 2 and FIG. 3, the inlet may be arranged in an acute angle. This allows a tool to be inserted through the inlet 25 into the working channel 19 towards the distal end of the insertion tube 3 of the endoscope 1. As can also be seen from FIGS. 2 and 3 the inlet 25 may comprise a check valve 27 closing the inlet to prevent leaking when no syringe 26 is attached, and preventing reflow into an attached syringe. The inlet is preferably a Luer lock port where the check valve 27 us actuated by the male Luer tip of the syringe, but other inlets may instead be used. Evidently, if a tool is to be inserted, the check valve 27 must allow the tool to pass, be it by a suitable construction, by being detachable, or be it in another manner known by the skilled person.

As mentioned, the liquid container 14 may be interchangeable. In that case, as can be seen in FIG. 7 the liquid container 14 is provided with an outlet port 17 adapted to engage and connect to an inlet port 24 of the working channel 19. Furthermore, the housing of the liquid container 14 is provided with an aperture 18 at the bottom allowing the piston rod 10 to enter the housing of the liquid container 14 and engage the piston 6.

The skilled person will understand that the above description of the sampling device is merely an illustration of preferred embodiments, and that the sampling device may be embodied in many different ways without departing from the scope of the invention. In particular the flow paths, connectors, valves etc. may be devised in many other ways.

The invention claimed is:

1. An endoscope comprising:
   a handle and an insertion tube extending from the handle;
   a working channel through which a liquid may pass, the working channel extending through the insertion tube;
   a suction connector;
   a sample container connector through which suction may be applied via the suction connector to the working channel, the sample container connector being integral with the handle and adapted to removably attach a sample container and establish a fluid connection therewith; and
   a diverter valve operable, in a first position, to apply the suction to the working channel through the sample container and, in a second position, to apply the suction to the working channel bypassing the sample container.

2. The endoscope of claim 1, wherein the sample container connector is adapted to penetrate at least one seal of the sample container.

3. The endoscope of claim 1, comprising a liquid container connected with the working channel and being an integral part of the endoscope.

4. The endoscope of claim 3, further comprising an actuator connected to the liquid container and operable to propel a liquid in the liquid container through said working channel.

5. The endoscope of claim 4, wherein the actuator for propelling the liquid through said working channel comprises a digitally displaceable actuator adapted to provide a force displacing the liquid.

6. The endoscope of claim 5, wherein the liquid container comprises a displaceable piston adapted to displace the liquid under the influence of the force provided by the actuator.

7. The endoscope of claim 6, wherein the digitally displaceable actuator is connected to a force transmitting kinematic chain adapted to transfer motion and force between the digitally displaceable actuator and the displaceable piston.

8. The endoscope of claim 1, the diverter valve comprising a valve actuator adapted to be operated using a single finger of a hand of an operator, the valve actuator located in a position on the endoscope where it is accessible and operable by the finger of the hand of the operator when the operator grips the handle with said hand.

9. The endoscope of claim 1, wherein the endoscope is adapted for single use and includes at least one material not suitable for sterilization.

10. A kit comprising
    an endoscope according to claim 1,
    a saline cartridge or a syringe for saline, and
    at least one sample container.

11. The endoscope of claim 1, wherein the diverter valve comprises a valve actuator located on the handle, the valve actuator being sized and configured to be operated by a single finger of a hand of an operator while the hand simultaneously grips the handle.

12. The endoscope of claim 11, wherein the valve actuator comprises a friction enhancing feature.

13. The endoscope of claim 12, wherein the friction enhancing feature comprises a surface including at least one of grooves or protrusions.

14. The endoscope of claim 1, wherein the diverter valve comprises a valve actuator located on the handle, the valve actuator being sized and configured to be operated by a single finger of a hand of an operator while the hand simultaneously grips the handle, the endoscope further comprising a valve which is normally closed and a push-button operable to open the valve, the valve disposed and establishing a fluid connection between the working channel and the diverter valve.

15. The endoscope of claim 1, wherein the sample container connector extends rigidly from the handle at a substantially perpendicular angle to a length of the endoscope.

16. The endoscope of claim 15, wherein the sample container connector is sized and configured to removably attached the sample container such that a length of the sample container is substantially parallel to the length of the endoscope.

17. A method of performing a lavage, the method comprising:
    providing an endoscope comprising: a handle and an insertion tube extending from the handle; a working channel through which a liquid may pass, the working channel extending through the insertion tube; a suction connector; and a sample container connector through which suction may be applied via the suction connector to the working channel, the sample container connector being integral with the handle and adapted to removably attach a sample container and establish a fluid connection therewith; and
    a diverter valve operable, in a first position, to apply the suction to the working channel though the sample container and, in a section position, to apply the suction to the working channel bypassing the sample container;
    inserting the sample container through an opening in the sample container;
    connecting the suction connector to a vacuum source;
    inserting the insertion tube of the endoscope into a body cavity;
    administering a saline solution through the working channel of the endoscope to the body cavity; and
    collecting a sample by drawing fluid from the body cavity through the endoscope and the sample container.

18. The method of claim 17, wherein drawing fluid from the body cavity through the endoscope and the sample container includes placing the diverter valve in the first position.

19. The method of claim 18, further comprising:
    placing the diverter valve in the second position; and
    removing the sample container from the endoscope.

20. The method of claim 19, wherein the method further comprises gripping the handle with a hand, wherein the diverter valve comprises a valve actuator located on the handle, and wherein placing the diverter valve in the second position comprises:

switching the diverter valve from the first position to the second position with a single finger of the hand.

21. The method of claim 17, wherein the endoscope further comprises a valve which is normally closed and a push-button operable to open the valve, the valve disposed and establishing a fluid connection between the working channel and the diverter valve, wherein drawing fluid from the body cavity through the endoscope and the sample container comprises, while the diverter valve is in the first position:

pushing the push-button to open the valve.

* * * * *